United States Patent
Van Lancker

(10) Patent No.: US 7,179,336 B2
(45) Date of Patent: Feb. 20, 2007

(54) PROCESS FOR PREPARING ALKALI- AND HEAT-STABLE SUGAR ALCOHOL COMPOSITIONS AND A SORBITOL COMPOSITION

(75) Inventor: Frank Van Lancker, Aalst (BE)

(73) Assignee: Tate & Lyle Europe N.V., Aalst (BE)

( * ) Notice: Subject to any disclaimer, the term of this patent is extended or adjusted under 35 U.S.C. 154(b) by 0 days.

(21) Appl. No.: 10/537,660

(22) PCT Filed: Dec. 30, 2002

(86) PCT No.: PCT/EP02/14916

§ 371 (c)(1),
(2), (4) Date: Jun. 6, 2005

(87) PCT Pub. No.: WO2004/058671

PCT Pub. Date: Jul. 15, 2004

(65) Prior Publication Data

US 2006/0144394 A1    Jul. 6, 2006

(51) Int. Cl.
*C07H 1/06*    (2006.01)
(52) U.S. Cl. .................. 127/46.2; 127/29; 536/127
(58) Field of Classification Search ............... 127/46.2, 127/29; 536/127
See application file for complete search history.

(56) References Cited

U.S. PATENT DOCUMENTS

| 5,773,604 | A  | * | 6/1998 | Lefevre et al. | ............. 536/104 |
| 6,451,123 | B1 | * | 9/2002 | Saska et al. | ............... 127/46.2 |

FOREIGN PATENT DOCUMENTS

| EP | 0711743 | 5/1996 |
| EP | 1095925 | 5/2001 |

OTHER PUBLICATIONS

Dabagov et al., "Chromatographic Separation of Polyhydric . . . ", Izvestiya Akademii Nauk SSSR, Seriya Khimicheskaya, No. 8, pp. 1308-1315, Aug. 1966.*

Fluka Chemika-BioChemika Catalogue 1995/96, pp. 1382-1383 (1995).*

* cited by examiner

*Primary Examiner*—David M. Brunsman
(74) *Attorney, Agent, or Firm*—James Creighton Wray

(57) ABSTRACT

The invention relates first of all to a process for preparing alkali- and heat-stable sugar alcohol compositions which exhibits an optical density lower than or equal to 0.100 in an S-test, in which a sugar alcohol composition is treated with a strong base anion exchange resin in the hydroxide form, at a temperature between 30° C. and 100° C. Second of all, the invention relates to a sorbitol composition.

17 Claims, No Drawings

PROCESS FOR PREPARING ALKALI-AND HEAT-STABLE SUGAR ALCOHOL COMPOSITIONS AND A SORBITOL COMPOSITION

This application claims the benefit of PCT Application No. PCT/EP2002/014916 filed Dec. 30, 2002, which is hereby incorporated by reference in its entirety.

BACKGROUND OF THE INVENTION

The invention relates on the one hand to a process for preparing alkali- and heat-stable sugar alcohol compositions which exhibits an optical density lower than or equal to 0.100 in an S-test. On the other hand, the invention relates to sorbitol compositions.

Alkali- and heat-stability of sugar-alcohols is important in all those applications where colour formation under these conditions must be prohibited. This is the case, e.g. where polyol compositions are used as humectants in tooth-pastes containing alkaline abrasives, as building blocks of polyether polyols, or as starters for preparing sorbitan esters. Colouring of end-products containing these polyols is often due to the presence of colour-forming precursors, including residual reducing sugars, in the sugar-alcohol compositions used.

This problem is quite well known and a number of solutions have already been proposed to improve alkali- and heat-stability of such polyol compositions.

In JP 63079844, a method is described in which an aqueous sugar alcohol solution is adjusted to a pH-value of between 8 and 13, followed by a (discontinuous) heating step at temperatures varying between 90° C. and 220° C. The resulting product is then purified by passing the polyol solution through a strongly acidic cation exchange resin, a strong base anion exchange resin and a mixed bed resin.

In EP 0 711 743, a similar process is disclosed in which the polyol composition is first stabilised by means of an oxidation, a fermentation or a caramelisation step, followed by a purification of the solution. The purification step is comparable to the one disclosed in JP 63079844.

In EP 1 095 925, a purification process is disclosed comprising a first treatment on a strong acid cationic exchange resin at a temperature below 50° C., preferably below 40° C., followed by a treatment on a strong basic anionic resin and a mixed bed resin.

Methods for removing aldehydes and other reactive impurities, and/or stabilising colour in glycerol and glycol aqueous solutions have been discussed in FR 1 546 472 and U.S. Pat. No. 6,187,973 respectively. In both cases, a strong base anion exchange resin in the hydroxide form was converted into the bisulphite form, in order to treat the aqueous polyol solutions.

The major disadvantage of the above-cited processes resides in their complexity. Indeed, first a chemical stabilisation step is needed, followed by a quite complicated purification step. During this stabilisation step, high pH-values are used. In addition, it is necessary to use quite high temperatures (>90° C.) and long reaction times to obtain the necessary stabilisation.( see JP63079844 and EP711743). This results in a rather important chemicals consumption during the chemical reaction, and later on, for the regeneration of the different ion exchange resins.

In addition, two separate steps are needed to arrive at the desired result. The equipment needed, therefore comprises a reactor to perform the stabilisation step, and at least two ion exchange resin batteries to perform the purification step.

In the case of the bisulphite-type resins, the use thereof proves to be inefficient when higher polyols such as pentitols, hexitols and/or hydrogenated starch hydrolysates are treated in the expectation of obtaining alkali- and heat stable products.

SUMMARY OF THE INVENTION

The purpose of the invention is to provide a simple process for preparing alkali- and heat-stable sugar alcohol compositions which exhibit an optical density lower than or equal to 0.100 in an S-test. This process results in a reduced consumption of chemicals and provides a combined one step alkaline stabilisation and decolourisation process. This one step process can be operated in a continuous matter.

This object is obtained by providing a process for preparing alkali- and heat-stable sugar alcohol compositions which exhibits an optical density lower than or equal to 0.100 in an S-test, in which a sugar alcohol composition is treated with a strong base anion exchange resin in the hydroxide form, at a temperature between 30° C. and 100° C.

DETAILED DESCRIPTION OF THE PREFERRED EMBODIMENTS

In a preferred process according to the invention, the sugar alcohol composition is fed to a column-system containing a strong base anion exchange resin in the hydroxide form with a volume throughput of $\leq 6$ bed volumes (BV)/hour.

"Bed volume" is hereby defined as the total volume of resin used during the stabilisation step, be it in a one column- or in a multiple column-system.

When a multiple column-system is used, at least part of the columns of the system is used in a regeneration mode, while the remaining columns are used in a service mode, comprising the steps of stabilisation and simultaneous decolourisation.

In a more preferred process according to the invention, the volume throughput is between 0.1 and 1 BV/hour.

Most preferably, the volume throughput is between 0.2 and 0.8 BV/hour.

Before treatment with the strong base anion exchange resin, said sugar alcohol composition has preferably a conductivity value less than 100 µS/cm, more preferably 50 µS/cm.

The strong base anion exchange resin preferably belongs to one of the categories:
  the thermally stable-type category;
  the styrenic type I, type II or type III; or
  the acrylic resin type.

When using a styrenic type I or type III, or an acrylic type resin, a column temperature is preferably used between 45° C. and 70° C.

When using a styrenic type II resin, a column temperature is preferably used less than 45° C.

When using a thermally stable resin, a column temperature is preferably used which is more than 75° C.

On the one hand, said sugar alcohol composition can be prepared by hydrogenating a starch hydrolysate, obtained from an acid conversion, a combined acid-enzymatic conversion or a multiple enzyme conversion of starch.

On the other hand, said sugar alcohol composition can be prepared by hydrogenating reducing sugars belonging to the categories of keto- or aldopentoses, keto- or aldohexoses, disaccharides or non-starch oligosaccharide mixtures.

In a preferred process according to the invention, said sugar alcohol composition has a pH-value between 8.5 and 9.5 when sorting from the strong base anion exchange resin.

The purpose of the invention is furthermore to provide a sorbitol composition which has a great alkali- and heat stability.

This purpose is obtained by providing a sorbitol composition containing at least 95% sorbitol on dry substance and exhibiting an optical density lower than 0.02, more preferably containing at least 99% sorbitol on dry substance and exhibiting an optical density of lower than 0.01.

These particular and unexpected sorbitol compositions can for instance be the result of the process of the invention. This doesn't exclude the fact that also other processes can be used for obtaining sorbitol compositions with the characteristics as mentioned above.

To prepare alkali- and heat-stable sugar alcohol compositions which exhibits an optical density lower than or equal to 0.100 in an S-test, which is within the terms of EP 0 711 743, a one step process is used in which all the colour precursors are eliminated, and the resulting sugar alcohol syrup become colourless and alkali- and heat-stable. Thereby surprisingly low reaction temperatures are used, i.e. between 30 and 100° C. These temperatures are sufficient to provide the desired result, as expressed by the S-value, when a strong base anion exchange resin in the hydroxyl form is used to treat the sugar alcohol compositions.

The S-test relies on a spectrophotmetric measurement applied to the products to be tested.

As used herein, the "S-test" is the following test procedure:

the aqueous polyol syrup to be tested is brought to a solids content of 40% by weight, if needed by concentration or by aqueous dilution;

to 5 ml of this solution are added 500 mf of sodium hydrogenecarbonate of ultrapure quality, sold, for example, under the name of RP Normapur™, analytical grade, by the company Prolabo, 65 Bd Richard Lenoir, Paris, France, and 250 mg of an aqueous solution containing 20% of ammonia;

the whole is mixed and heated for 2 hours on a steam bath at 100° C. without stirring being applied;

the solution is brought to 20° C. and the optical density of the solution thus obtained is measured at a wavelength of 420 nm by virtue of a spectrophotometer such as that marketed by Perkin-Elmer under the trademark Lambda 5 UV/VIS Spectrophotometer.

In a process according to the invention, a single or multiple column-system is used, containing a strong base anion exchange resin in the hydroxide form with a volume throughput of =<6 bed volumes (BV)/hour.

An advantageous continuous multiple column-system for this invention is known as an ISEP- or as a CSEP-configuration. Thereby, a part of the columns in the system is used in the regeneration mode, while the remaining columns are used for the stabilisation and simultaneous decolourisation of the substrate, i.e. a service mode. Thereby, a column operating in the service mode will become deactivated, after that a certain quantity of substrate is processed by that column. This deactivation can be observed by monitoring the pH of the syrup leaving that column. This "exhausted" column is then switched to the regeneration mode and replaced by a regenerated column. The volume throughput is preferably between 0.1 and 1 BV/hour, more preferably between 0.2 and 0.8 BV/h.

The strong base anion exchange resins used in this invention belong to the styrenic type I, type II, or type III categories, to the acrylic resin type, and to the thermally stable-type categories.

The styrenic type I-category comprises resin types such as Amberlite IRA404, FP A90 and Amberjet 4400, Dowex Marathon 11 and Lewatit M500.

A typical representative of the type II-resins is the styrenic resin type Dowex 22.

A typical representative of the type III-resins is the styrenic resin type Purolite A555.

The acrylic resin type categorie is represented e.g. by Amberlite IRA458 and Amberlite FP A98.

In the category of the thermally stable strong base anion resins, Diaion TSA1200 is a typical example.

When using styrenic type I or type III resins, or acrylic type resins, column temperature is preferably between 45° C. and 70° C.

When using styrenic type II resins, column temperature is preferably <45° C.

When using thermally stable resins, column temperature is preferably >75° C.

The sugar alcohol composition is obtained via the hydrogenation of reducing sugar compositions. Typical reducing sugar compositions are starch hydrolysates, but also other reducing sugars including keto- and aldopentoses, keto- and aldohexoses, disaccharides (e.g. lactose, maltose, isomaltose, isomaltulose) and non-starch oligosaccharide mixtures are covered by this term. The term starch hydrolysates refers to those compositions obtained via an acid conversion, a combined acid-enzymatic conversion, or a multiple enzyme conversion of starch, including chemical or enzymatic isomerisation. Typical representatives here are maltodextrins, "standard" glucose syrups, maltose syrups, high DE conversion syrups such as 96DE and 99DE glucose syrups, isoglucoses and crystallisation mother liquors. The starch may be of cereal, tuber root or leguminous origin.

The sugar alcohol substrate needing a stabilisation treatment, preferably has a conductivity value <100 S/cm, more preferable <50 µS/cm, before treatment with the strong base anion exchange resin. Such sugar alcohol compositions can be obtained when using a noble metal hydrogenation catalyst, for example Ru, Pt or Pd; or by first removing dissolved residual metal ions from the substrate, in those cases where transition metals such as for example Ni, Co, Cu or Fe are used as the catalysts.

The processed, colour-stable sugar alcohols thus obtained typically have a pH-value varying between 8.5 and 9.5 when sorting from the strong base anion exchange resin. These sugar alcohol compositions can then be used as such or further processed by means of a mixed bed resin or a weak acid cation exchange resin, thereby providing a syrup having a pH=4–7, preferably pH=5–6.5.

Sorbitol compositions with great alkali- and heat stability can be obtained by the process of the invention as described above. This doesn't exclude the fact that also other processes can be used for obtaining such particular and unexpected sorbitol compositions.

The sorbitol composition comprise at least 95% sorbitol on dry substance and exhibits an optical density lower than 0.02.

In a more preferred embodiment of the invention, the sorbitol composition comprise at least 99% sorbitol on dry substance and exhibits an optical density of lower than 0.01.

In order to illustrate this invention, a number of examples are provided hereunder.

EXAMPLES

Comparative Example 1

A sorbitol syrup containing 96% sorbitol and showing an S-value of 1.10 before stabilisation is submitted to an alkaline heat treatment. Thereby the pH is brought to pH=11.2 with 1N NaOH and the syrup is heated for 2 hours at different temperatures, followed by a refining step. After refining the stability of the thus processed syrup is measured by means of the S-test. Thereby it is clearly illustrated that sufficiently high temperatures are needed to obtain sufficient stabilisation within a reasonable time. The effect of the stabilisation conditions is clearly illustrated in the following table.

| Stabilisation conditions | S-value |
| --- | --- |
| Unstabilised | 1.10 |
| 2h at 80° C. and pH = 11.2 | 0.35 (is > 0.1) |
| 2h at 100° C. at pH = 11.2 | 0.021 |

Comparative Example 2

In this example it is shown that the use of strong base anionic exchange resins, in the sulphite form, is not suitable to obtain alkali- and heat-stable polyols, comparable with the polyols disclosed in EP 0 711 743.

A strong base anion exchange resin in the hydroxide form was thereby converted to the bisulphite form by passing a 2 mol/l solution of $NaHSO_3$ through a bed of the resin until the bisulphite inlet and outlet concentrations were essentially the same.

This resin was then washed with 10 volumes of water per volume of resin.

A unrefined sorbitol solution, having a S-value of 0.85 (as determined by the S-test of EP711743) was then passed through the bisulphite-treated resin at ambient temperature.

The treated solutions did not fulfil the requirements set forward by EP 0 711 743, in order to claim alkali/heat stability for these polyols, as illustrated in table 1.

TABLE 1

Treatment of sorbitol by anion exchange resin in bisulphite form:

| Sorbitol (99.5%) | S-value |
| --- | --- |
| Untreated | 0.85 |
| Dowex 22 (1) | 0.72 |
| Lewatit M500 (1) | 0.64 |

(1): Dowex 22(type II) and Lewatit M500 (type I) are both strong base anion exchange resins, transformed in the bisulphite form as described above.

Example 1

Four different columns are filled with 100 ml of a different strong base anionic exchange resin in the hydroxide form.

The resins used are: Amberlite FPA 90, Amberlite IRA 458, Amberjet 4400 and Purolite A555.

The operating temperature for the columns containing Amberlite FPA90 and Amberjet 4400 is 60° C. The operating temperature for the columns containing Amberlite IRA458 and Purolite A555 is 55° C.

The unrefined sorbitol syrup used is obtained by the hydrogenation of a 96 DE-glucose syrup and has a concentration of about 50% d.s. The S-value of the syrup is 1.11.

The syrup is passed through the columns at 0.33 BV/hour. The S-value of the processed substrate is determined in the mixture of the collected volumes of the first 25 bed volumes.

TABLE 2

Sorbitol syrup stabilisation via strong base anionic resin treatment as expressed by their S-value:

| Sorbitol syrup substrate | S-value |
| --- | --- |
| untreated | 1.11 |
| Amberlite FPA 90 | 0.042 |
| Amberlite IRA 458 | 0.016 |
| Amberjet 4400 | 0.016 |
| Purolite A555 | 0.014 |

Example 2

The same procedure as in example 1 was followed. The substrate treated now is sorbitol syrup, obtained by the hydrogenation of a D99 dextrose syrup. The sorbitol syrup has a 99.4% sorbitol content and an S-value of 0.87 before stabilisation.

This syrup is again passed through the columns at 0.33 BV/hour. The processed sorbitol syrup is collected. A mixed sample corresponding to the mixture of the first 30 bed volumes is submitted to the S-test.

TABLE 3

D99 Sorbitol syrup stabilisation via strong base anionic resin treatment as expressed by their S-value:

| D99 Sorbitol syrup substrate | S-value |
| --- | --- |
| untreated | 0.87 |
| Amberlite FPA 90 | 0.007 |
| Lewatit M500 | 0.006 |
| Purolite A555 | 0.007 |

Example 3

The same procedure as in example 1 was followed. The substrate treated now is a maltitol syrup, obtained by the hydrogenation of a high maltose syrup containing about 65% maltose, 8% glucose and 20% maltotriose. The maltitol syrup has an S-value of 2 before refining.

This syrup is again passed through the columns at 0.33 BV/hour. The processed maltitol syrup is collected. A mixed sample corresponding to the mixture of the first 25 bed volumes is submitted to the S-test.

TABLE 4

Maltitol syrup stabilisation via strong base anionic resin treatment as expressed by their S-value:

| Maltitol syrup substrate | S-value |
| --- | --- |
| Untreated | 2.0 |
| Amberlite FPA 90 | 0.065 |
| Amberlite IRA 458 | 0.08 |
| Amberjet 4400 | 0.11 |
| Purolite A555 | 0.09 |

This example shows that the substrate composition, the original S-value of the substrate, as well as the ion exchange resin used, may affect the refining capacity.

Example 4

One column is filled with 100 ml of a strong base thermally stable anion exchange resin (Diaion TSA1200). The substrate treated is a maltitol syrup, obtained by the hydrogenation of a high maltose syrup containing about 65% maltose, 8% glucose and 20% maltotriose. The maltitol syrup has an S-value of 2.2 before refining. The syrup (50% d.s.) is passed, at 90° C., through the column at a speed of 2 BV/hour. The evolution of the S-value as a function of the number of bed volumes processed is given in the next table.

| BV treated | S-value |
| --- | --- |
| 5 | 0.012 |
| 10 | 0.013 |
| 20 | 0.022 |
| 30 | 0.028 |
| 40 | 0.037 |

Example 5

One column is filled with 100 ml of a strong base styrenic type II anion exchange resin (Dowex 22). The substrate treated is a sorbitol syrup (96% sorbitol), obtained by the hydrogenation of a 96DE glucose syrup. The sorbitol syrup has an S-value of 0.81 before stabilisation.

The syrup (50% d.s.) is passed, at 40° C., through the column at a speed of 0.2 BV/hour. After 24 hour the S-value of the collected volume was determined. The value of the collect volume was S=0.036.

Example 6

In this example a multiple column system is used to refine a maltitol syrup having a S-value of 2.2 before treatment. The maltitol syrup is obtained by the hydrogenation of a high maltose syrup containing about 65% maltose, 8% sorbitol and 20% maltotriose.

Four columns are each filled with 100 ml Amberlite IRA458 resin in the hydroxyl form. Three out of four columns are connected in series. The maltitol syrup is passed through these three columns at a speed of 100 ml/h. (0.33 BV/h-300 ml resin in use). The temperature of the columns is 55° C. The treated syrup is collected in fractions of 1 liter, and of each such fraction the S-value is determined. In a spot sample, at the outlet of the first column, the pH is measured on the moment that a 1 liter fraction is collected at the outlet of the third (last) column of the stabilisation cycle. When the pH shows a significant drop compared to the pH of the previous sampling, then:

- this first column (n°1) is taken out of service and is regenerated
- the second column (n°2) now becomes the first column, and receives the substrate to be treated,
- the third column (n°3) becomes the second column,
- the column that was stand-by (n°4) now becomes the third column in the series.

This stabilisation process is continued until column n°2, now the first column, shows a significant pH-drop.

The results of such a carrousel process are given in the next table.

TABLE 4

Continuous carrousel process for stabilising maltitol syrup

| Columns in service | Syrup processed (I) | pH outlet first column | S-value last column outlet |
| --- | --- | --- | --- |
| (1)(2)(3) | 1.0 | 9.3 | 0.026 |
|  | 2.0 | 9.1 | 0.032 |
|  | 3.0 | 8.8 | 0.042 |
|  | 4.0 | 8.2 | 0.053 |
| (2)(3)(4) | 5.0 | 9.1 | 0.036 |
|  | 6.0 | 9.0 | 0.044 |
|  | 7.0 | 8.7 | 0.053 |
|  | 8.0 | 8.2 | 0.064 |
| (3)(4)(1) | 9.0 | 9.1 | 0.038 |
|  | 10.0 | 9.0 | 0.047 |
|  | 11.0 | 8.7 | 0.058 |
|  | 12.0 | 8.0 | 0.067 |

The ivention claimed is:

1. Process for preparing alkali- and heat-stable sugar alcohol compositions which exhibits an optical density lower than or equal to 0.100 in an S-test, characterised in that a sugar alcohol composition is treated with a strong base anion exchange resin in the hydroxide form, at a temperature between 30° C. and 100° C.

2. Process according to claim 1, characterised in that in said process the sugar alcohol composition is fed to a column-system containing a strong base anion exchange resin in the hydroxide form with a volume throughput of =6 bed volumes (BV)/hour.

3. Process according to claim 2, characterised in that a single column-system is used.

4. Process according to claim 2, characterised in that a multiple column-system is used, in which at least part of the columns of the system is used in a regeneration mode, while the remaining columns are used in a service mode, comprising the steps of stabilisation and simultaneous decolourisation.

5. Process according to claim 2, characterised in that the volume throughput is between 0.1 and 1 BV/hour.

6. Process according to claim 5, characterised in that the volume throughput is between 0.2 and 0.8 BV/hour.

7. Process according to claim 1, characterised in that said sugar alcohol composition has a conductivity value less than 100 μS/cm before treatment with the strong base anion exchange resin.

8. Process according to claim 7, characterised in that said sugar alcohol composition has a conductivity less then 50 μS/cm before treatment with the strong base anion exchange resin.

9. Process according to claim 1, characterised in that said strong base anion exchange resin belongs to the thermally stable-type category.

10. Process according to claim 9, characterised in that when using a thermally stable resin, a column temperature is used which is more than 75° C.

11. Process according to claim 1, characterised in that said strong base anion exchange resin is of the styrenic type I, type II or type III.

12. Process according to claim 11, characterised in that when using a styrenic type II resin, a column temperature is used which is less than 45° C.

13. Process according to claim 1, characterised in that said strong base anion exchange resin is of the acrylic resin type.

14. Process according to claim 1, characterised in that when using a styrenic type I or type III, or an acrylic type resin, a column temperature is used between 45° C. and 70° C.

15. Process according to claim 1, characterised in that said sugar alcohol composition is prepared by hydrogenating a starch hydrolysate, obtained from an acid conversion, a combined acid-enzymatic conversion or a multiple enzyme conversion of starch.

16. Process according to claim 1, characterised in that said sugar alcohol composition is prepared by hydrogenating reducing sugars belonging to the categories of keto- or aldopentoses, keto- or aldohexoses, disaccharides or non-starch oligosaccharide mixtures.

17. Process according to claim 1, characterised in that said sugar alcohol composition has a pH-value between 8.5 and 9.5 when sorting from the strong base anion exchange resin.

* * * * *

UNITED STATES PATENT AND TRADEMARK OFFICE
CERTIFICATE OF CORRECTION

PATENT NO. : 7,179,336 B2 Page 1 of 1
APPLICATION NO. : 10/537660
DATED : February 20, 2007
INVENTOR(S) : Frank Van Lancker It is certified that error appears in the above-identified patent and that said Letters Patent is hereby corrected as shown below:

Column 8, Line 33 (Claim 2): Delete "=" and substitute -- < or = --.

Signed and Sealed this

Thirtieth Day of September, 2008

JON W. DUDAS
*Director of the United States Patent and Trademark Office*